(12) United States Patent
Griffiths et al.

(10) Patent No.: US 7,407,948 B2
(45) Date of Patent: Aug. 5, 2008

(54) PHOTOSENSITISERS AND THEIR USES

(75) Inventors: John Griffiths, Leeds (GB); Stephen Anthony Gorman, Colne (GB); Andrea Bell, Greengates (GB)

(73) Assignee: Photopharmica Limited, Leeds (GB)

( * ) Notice: Subject to any disclaimer, the term of this patent is extended or adjusted under 35 U.S.C. 154(b) by 0 days.

(21) Appl. No.: 11/723,522

(22) Filed: Mar. 20, 2007

(65) Prior Publication Data

US 2007/0197494 A1 Aug. 23, 2007

(51) Int. Cl.
C07D 421/02 (2006.01)
A61K 31/55 (2006.01)
(52) U.S. Cl. .......................................... 514/183; 544/1
(58) Field of Classification Search ...................... 544/1; 514/183
See application file for complete search history.

(56) References Cited

FOREIGN PATENT DOCUMENTS

| DE | 3125296 A1 | 1/1983 |
|---|---|---|
| EP | 0 068 425 B1 | 1/1983 |
| GB | 2 083 488 A | 3/1982 |
| GB | 2083488 A * | 3/1982 |
| WO | WO 01/49328 A1 | 7/2001 |
| WO | WO 02/096896 A1 | 12/2002 |

OTHER PUBLICATIONS

Cecil Textbook of Medicine (20th Edition, vol. 2, 1996, pp. 1739-1747).*
T.G. Brien (1972) Selenium Labelled Toluidine Blue as an Agent for Parathyroid Scanning, Acta Radiologica: Therapy, Physics, Biology, 11(4):312-320 and Chemical Abstract No. 78:54948.
Cincotta et al. (1993) Phototoxicity, Redox Behavior, and Pharmacokinetics of Benzophenoxazine Analogues in EMT-6 Murine Sarcoma Cells, Cancer Research, 53(11):2571-2580 and Chemical Abstract No. 119:90259.
Georgakoudi et al. (1998) Effects of the Subcellular Redistribution of Two Nile Blue Derivatives on Photodynamic Oxygen Consumption, Photochem. Photobiol., 68(1):115-122.
Granick et al. (1940) Semiquinones of Oxazines, Thiazines and Selenazines, JACS, 62:1802-1810.
Groves (1974) Synthesis of Seleno-Toluidine Blue, J. Med. Chem., 17(8):902-904 and Chemical Abstract No. 83:37393.
Harris et al, (2004) An Investigation to the Potential of Phenothiazinium-Based Photo-Sensitisers to Act as PDT Agents, Photodiag. Photodyn. Ther., 1:231-239.
Karrer (1916) Uber Selenazin-Farbstoffe, Chem. Ber. 49:597-603.
Leyck et al. (1993) Antioxidant and Anti-inflammatory Activities of Selenomethylene Blue, Agents and Actions, Spec. Conf. Issue, 38:C143-C145 and Chemical Abstract No. 119:108584.
Vogelmann et al (1976) Photochemical Investigations of Oxazine, Thiazine and Selenazine Dyes, Photochem. Photobiol., 23:383-390.
Wainwright (2000) Methylene Blue Derivatives—Suitable Photoantimicrobials for Blood Product Disinfection?, Intern. J. Antimicr. Agents, 16:381-394.
Wu et al. (1995) Interference of Heavy-Atom With Magnetic Spin Effects in Spin-Correlated Micellar Radical Pairs, Molecular Physics, 84(5):981-994 and Chemical Abstract No. 123:198178.

* cited by examiner

Primary Examiner—Kahsay T Habte
(74) Attorney, Agent, or Firm—Morgan, Lewis & Bockius LLP

(57) ABSTRACT

Phonoselenazinium compounds of Formula (1):

Formula (1)

$$\left[ \begin{array}{c} R1 \quad\quad R4 \\ R2 \underset{A}{\overbrace{\phantom{XXXXX}}} N \underset{}{\overbrace{\phantom{XXXXX}}} R5 \\ \phantom{R2} \underset{R3}{\overbrace{\phantom{XXXXX}}} \underset{+}{Se} \underset{R6}{\overbrace{\phantom{XXXXX}}} B \end{array} \right]_p Y^{p-}$$

and their use in photodynamic therapy (PDT), particularly as anti-infectives, as anti-cancer agents, and as sterilising agents both for direct use and in combination with a polymer, wherein: A and B are each independently selected from:

—N(piperidine-Q,Z), —N(morpholine-Q,Z), —N(pyrrolidine-Q), —N(pyrrolidine-Q), —N(azepane), and —CHR⁷R⁸;

7 Claims, No Drawings

PHOTOSENSITISERS AND THEIR USES

FIELD OF THE INVENTION

This invention relates to biologically active phenoselenazinium compounds, and compositions and medicaments comprising them, their use in in vivo photodynamic therapy (PDT) particularly their use as anti-infectives, as anti-cancer agents and as sterilising agents both for direct use and in combination with a polymer.

BACKGROUND OF THE INVENTION

Certain benzo[α]phenoselenazinium compounds are known (Cancer Research 1993, Vol 53 (11), p 2571-2580) and their performance was compared with S containing analogues in use for treatment of murine sarcoma tumours in vitro, along with their ability to yield singlet oxygen. However, a compound's ability to yield singlet oxygen does not provide a reliable way to predict whether or not a compound will be effective in therapy.

For example, a study of chalcogenopyrylium dyes as potential sensitizers for the photodynamic therapy of cancer in Journal of Medicinal Chemistry (1999), 42(19), 3953-3964 concluded that the presence of a sulphur, selenium, or tellurium heteroatom in a molecule had no predictable impact on its toxicity. Further in Photochemistry and Photobiology (1998), 67(6), 612-625 the cytotoxic effects of Nile blue selenium (EtNBSe) were compared with those of Photofrin (a drug that is degraded via a $^1O_2$-mediated mechanism) it concluded that the lower threshold $^1O_2$ dose and the higher extinction coefficient and higher $^1O_2$ yield for EtNBSe does not necessarily result in improved photodynamic effects.

Seleno-methylene blue and its properties as an anti-oxidant and anti-inflammatory is discussed in Agents and Actions 1993, Vol 38, C143-C145 and concludes that the selenium analogue does not exhibit a different anti-oxidant or anti-inflammatory profile versus the sulphur compound but does exhibit increased inhibitory activity of iron-induced hepatic lipid peroxidation in vitro and ex vivo.

The present invention seeks to provide biologically active phenoselenazinium compounds suitable for use in in vivo photodynamic therapy (PDT), particularly as anti-infectives and as anti-cancer agents. Further the present invention seeks to provide sterilising agents both for direct use and in combination with polymers.

SUMMARY OF THE INVENTION

According to the present invention there is provided a phenoselenazinium compound of Formula (1):

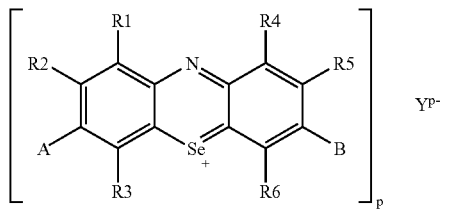

Formula (1)

wherein:
$R^1$-$R^6$ each independently is selected from H, optionally substituted alkyl, optionally substituted alkoxy, F, Cl, Br and I;

A and B each independently is selected from:

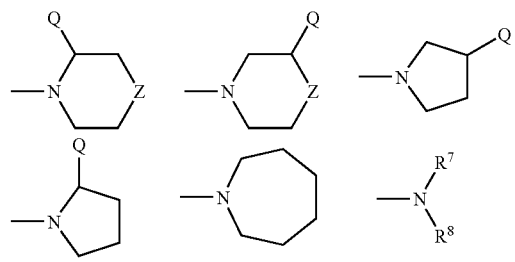

in which:
Q is selected from H and optionally substituted alkyl;
Z is selected from $C(R^a)_2$, O, S, $SO_2$, $NR^a$ in which each $R^a$ independently is selected from H and optionally substituted alkyl;
$R^7$ and $R^8$ each independently is selected from H and optionally substituted alkyl;
Y is a counteranion; and
p is 1, 2 or 3,
except for 3,7-bis(N,N-dimethylamino)-phenoselenazin-5-ium chloride and 3,7-diamino-phenoselenazin-5-ium chloride and the corresponding bromides and iodides, and the compound in which $R^1$ to $R^4$, and $R^6$ are all H, $R^5$ is methyl, A is $NMe_2$ and B is $NH_2$.

DETAILED DESCRIPTION

It is preferred that the compounds of Formula (1) exclude 3,7-bis(4-methyl-1-piperazinyl) phenoselenazinium dichloride and 3,7-bis(4-methyl-1-piperazinyl) phenoselenazinium bromide, compounds in which both A and B are $NMe_2$, and a compound of Formula (1) in which $R^1$-$R^6$ are all H, p is 1, Y is a counteranion, A and B=$NH_2$.

The alkyl groups represented by $R^1$ to $R^8$ preferably contain from 1-12 carbon atoms, more preferably from 1-10 carbon atoms, especially from 2-8 carbon atoms.

In a preferred sub group of compounds of Formula (1) A and B each independently is selected from —$NR^7R^8$ and the alkyl groups represented by $R^1$ to $R^8$ contain from 2-6 carbon atoms.

In a further preferred sub group of compounds of Formula (1) A and B each independently is selected from —$NR^7R^8$, the alkyl groups represented by $R^1$ to $R^6$ contain from 1-6 carbon atoms and the alkyl groups represented by $R^7$ to $R^8$ contain from 2-5 carbon atoms.

In a further preferred sub group of compounds of Formula (1) the groups represented by $R^1$ to $R^6$ are each independently selected from H or alkoxy, A and B each independently is selected from —$NR^7R^8$ and $R^7$ and $R^8$ each independently is an alkyl group containing from 2-5 carbon atoms.

In a further preferred sub group of compounds of Formula (1) the groups represented by $R^1$ to $R^6$ are H, A and B each independently is selected from —$NR^7R^8$ and $R^7$ and $R^8$ each independently is an alkyl group containing from 2-5 carbon atoms.

The alkyl groups represented by $R^a$ or Q preferably contain from 1-12 carbon atoms, more preferably from 1-6 carbon atoms, especially from 1-4 carbon atoms.

Where any one of $R^1$-$R^8$, $R^a$ or Q is optionally substituted alkyl the optional substitutents are preferably selected from aryl, particularly Ph; F; Cl; Br; I; OH; $OC_{1-4}$-alkyl, particularly $OCH_3$, $OC_2H_5$, $OC_3H_7$; CN; $OCOC_{1-4}$-alkyl, particularly OCOCH$_3$; optionally substituted C$_{3-6}$-cycloalkyl, particularly cyclohexyl, methyl-substituted cyclohexyl, cyclopentyl, and methyl-substituted cyclopentyl; COOH; COOC$_{1-4}$-alkyl; SO$_3$H;

The alkyl groups represented by R$^1$-R$^8$, R$^a$ or Q may be straight or branched chain and may optionally include C—C double or triple bonds. Further where there are more than 3 carbon atoms in alkyl groups represented by R$^1$-R$^8$, R$^a$ or Q the alkyl groups may be cyclic. Where the alkyl group represented by R$^1$-R$^8$, R$^a$ or Q is a cyclic group it preferably contains from 3 to 8 carbon atoms, more preferably from 4 to 6 carbon atoms and especially 6 carbon atoms. These cyclic hydrocarbon groups may include one or more unsaturated links, they may be optionally substituted and may optionally include a heteroatom such as nitrogen.

The alkoxy groups represented by R$^1$ to R$^6$ preferably contain from 1-12 carbon atoms, more preferably from 1-10 carbon atoms, especially from 1-6 carbon atoms.

In a preferred sub group of compounds the alkoxy groups represented by R$^1$ to R$^6$ contain from 1-4 carbon atoms. Where any one of R$^1$-R$^6$ is optionally substituted alkoxy the optional substitutents are preferably selected from any of the groups described above as optional substitutents for the alkyl groups represented by R$^1$-R$^8$ R$^1$-R$^6$ each independently is preferably selected from H, CH$_3$, OCH$_3$, F, Cl, Br and I, more preferably H, OCH$_3$, F, Cl, Br and I, and especially H and OCH$_3$.

Where A and B are both NR$^7$R$^8$, R$^7$ and R$^8$ each independently preferably is selected from H and C$_{1-6}$-alkyl optionally substituted by Ph, F, Cl, Br, I, OH, OCH$_3$, OC$_2$H$_5$, OC$_3$H$_7$, CN, OCOCH$_3$, cyclohexyl, methyl-substituted cyclohexyl, cyclopentyl, and methyl-substituted cyclopentyl, more preferably C$_{1-6}$-alkyl optionally substituted by Ph, F, Cl, Br, I, OH, OCH$_3$, OC$_2$H$_5$, OC$_3$H$_7$, CN, OCOCH$_3$, cyclohexyl, methyl-substituted cyclohexyl, cyclopentyl, and methyl-substituted cyclopentyl, more preferably R$^7$ and R$^8$ each independently is unsubstituted C$_{1-6}$-alkyl and especially R$^7$ and R$^8$ each independently is unsubstituted C$_{2-6}$-alkyl and most preferably C$_{2-5}$-alkyl.

Q is preferably H or CH$_3$

Z is preferably selected from CH$_2$, O, S, SO$_2$, NH, NCH$_3$, NC$_2$H$_5$, NCH$_2$CH$_2$OH and NCOCH$_3$.

R$^a$ is preferably selected from H, CH$_3$, C$_2$H$_5$, CH$_2$CH$_2$OH and COCH$_3$.

Y may be an organic or inorganic counteranion and is preferably selected from F$^-$, Br$^-$, Cl$^-$, I$^-$, NO$_3^-$, SCN$^-$, ClO$_3^-$, ClO$_4^-$, IO$_3^-$, BF$_4^-$, HSO$_4^-$, H$_2$PO$_4^-$, CH$_3$SO$_4^-$, N$_3^-$, SO$_4^{2-}$, HPO$_4^{2-}$, PO$_4^{3-}$, acetate, lactate, citrate, tartrate, glycolate, glycerate, glutamate, β-hydroxyglutamate, glucouronate, gluconate, malate and aspartate. In the compounds of Formula (1) where one or both of A and B is

one or both of R$^7$ and R$^8$ together with the nitrogen atom to which they are attached may form an optionally substituted 5-, 6- or 7-membered ring.

In compounds of Formula (1) the groups R$^1$ and R$^2$ and/or R$^4$ and R$^5$ together with the carbon atoms to which they are attached may form an optionally substituted 5-, 6- or 7-membered ring, it is preferred that the following compound is excluded, that in which R$^1$-R$^3$ and R$^6$ are all H, R$^4$ and R$^5$ form a 6-membered ring, p is 1, Y is chloro, A is NEt$_2$ and B is NHEt.

The rings formed from one or both of R$^7$ and R$^8$ together with the nitrogen atom to which they are attached and from the groups R$^1$ and R$^2$ and/or R$^4$ and R$^5$ together with the carbon atoms to which they are attached may be saturated or unsaturated.

R$^1$, R$^2$, R$^4$ and R$^5$ are preferably open chain substitutents.

The optional substitutents for the optionally substituted 5-, 6- or 7-membered rings formed from R$^7$ and R$^8$ together with the nitrogen atom to which they are attached and formed from the groups R$^1$ and R$^2$ and/or R$^4$ and R$^5$ together with the carbon atoms to which they are attached may be selected from any of those substitutents described above for R$^1$ In the compounds of Formula (1) it is preferred that both A and B each independently is of the formula:

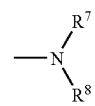

in which R$^7$ and R$^8$ each independently is optionally substituted, open chain alkyl. In the compounds of Formula (1) it is further preferred that R$^1$-R$^6$ each independently is selected from H or alkoxy.

In a first embodiment of the present invention in the compounds of Formula (1) R$^1$-R$^6$ each independently is selected from H or methoxy;

A and B each independently is

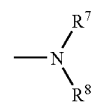

in which R$^7$ and R$^8$ each independently is C$_{2-5}$-alkyl; and

Y is a counteranion.

In a second embodiment of the present invention in the compounds of Formula (1) R$^1$-R$^6$ each independently is selected from H or methoxy; A and B are different and each independently is

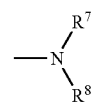

in which R$^7$ and R$^8$ each independently is C$_{2-5}$-alkyl; and Y is a counteranion.

Especially preferred compounds of Formula (1) are those described below as Compounds 1, 2, 3, 4, 5, 6 and 7.

Phenoselenazinium compounds are blue dyes with maximum absorption at wavelengths typically between 600-700 nm.

The compounds of Formula (I) in which A=B may be prepared by reaction of selenium monochloride, in an organic liquid such as toluene, with a diphenylamine or substituted diphenylamine at an elevated temperature such as the boiling point of the reaction mixture. The intermediate phenoselenazine may be purified by steam distillation to remove unreacted diphenylamine followed by any convenient purification means such as recrystallisation from an organic liquid such as toluene. The phenoselenazine is reacted, preferably in an inert atmosphere, with bromine in an organic liquid, such as glacial acetic acid. The dibromo compound formed may be isolated by any convenient means such as by pouring the reaction mixture into water and collecting the resulting precipitate by filtration. The dibromo compound is preferably dried before reacting with a suitable nitrogen containing compound in an organic liquid such as dichloromethane preferably in an inert atmosphere. For example where A and B are both —$NR^7R^8$ and $R^7$ and $R^8$ are alkyl then a suitable nitrogen containing compound is a di-N-alkylamine. When the reaction is complete, typically in about 10-12 hours the product may be isolated by shaking the reaction mixture with water, separating, shaking with a dilute aqueous acid solution, such as 1% hydrobromic acid, separating and shaking with water. The organic phase is separated and dried over a drying agent such as anhydrous magnesium sulphate. The product may be purified by any convenient means such as by flash chromatography using silica gel 60 A and a mobile phase of an organic liquid such as chloroform with an increasing amount of an alternative organic liquid such as methanol. The phenoselenazinium salt may be isolated from the eluates by precipitation with an organic liquid such as petroleum spirit.

Alternatively the compounds of Formula (I) in which A=B may be prepared via the intermediate diiodo compound which is made by reacting phenoselenazine with iodine in a suitable organic liquid, such as a haloalkane (for example chloroform). The diiodo compound may be isolated by filtration, washing with chloroform to remove iodine and drying.

Compounds of Formula (1) in which A≠B may be prepared as follows:

a) Phenoselenazine in an organic liquid such as chloroform is cooled to below 5° C. and a solution of iodine in chloroform added. The solid formed may be collected by filtration, washed with chloroform until free of iodine and then kept at room temperature under vacuum overnight to give phenoselenazin-5-ium tetraiodide hydrate.

b) the phenoselenazin-5-ium tetraiodide hydrate in an organic liquid such as methanol is added to a solution of a nitrogen containing compound for example an amine $R^7R^8NH$ (in which $R^7$ and $R^8$ are as defined above). The reaction mixture is stirred overnight, reduced by evaporation and left to cool. The solid formed may be collected by filtration, washed with an organic liquid such as diethyl ether and dried.

c) a solution of a different second solution of a nitrogen containing compound such as an amine $R^7R^8NH$ (in which $R^7$ and $R^8$ are as defined above) in an organic liquid such as dichloromethane is added to a solution of the solid from b) above in an organic liquid such as dichloromethane. Optionally triethylamine in an organic liquid such as dichloromethane may be added before the second amine. The reaction mixture is stirred overnight, the organic layer washed with dilute hydrochloric acid and water, separated and dried ($MgSO_4$). The majority of the solvent is evaporated and diethyl ether added to precipitate the product which is collected by filtration, washed with diethyl ether and dried. Further purification of the product, if necessary, may be by flash chromatography as described above.

According to a further feature of the present invention there is provided a composition comprising one or more compounds of Formula (1) together with a diluent or excipient. It is envisaged that the compositions may comprise one or more compounds of Formula (1).

The compounds of Formula (1) may be formulated into a variety of pharmaceutically compositions and medicaments which contain the compounds of Formula (1) and pharmaceutically acceptable carriers, excipients, adjuvants (each selected for certain characteristics that permit optimal formulation of a pharmaceutical composition). The compositions and medicaments include liposomes, nanoparticles, colloidal suspensions, micelles, microemulsions, vesicles and nanospheres.

The compositions and medicaments may also comprise further components such as conventional delivery vehicles and excipients including solvents such as alcohols (for example ethanol, polyethylene glycol, glycerol or n-butanol), dimethyl sulphoxide, water, saline, solubilisers such as castor oil derivatives for example ethoxylated castor oils like Cremophor EL (trade mark BASF AG), Tween (trade mark, ICI Americas Inc.) types, Solutol HS15, Unguentum (trade mark, Merck KGaA), isotonising agents such as urea, glycerol, aminoethanol, propylene glycol, pH regulators, dyes, gelling agents, thickeners, buffers, and combinations thereof. The compositions may also optionally include other carriers, stabilizers, preservatives or adjuvants. For typical examples of these classes of compounds, see *Remington: The Science and Practice of Pharmacy*, Lippincott, Williams & Wilkins (2005), which is incorporated by reference in its entirety.

The compositions and medicaments may comprise further active pharmaceutical ingredients.

Typically the compositions and medicaments are prepared by mixing a compound of Formula (1) with one or more pharmaceutically acceptable carriers at an appropriate temperature, typically from 15° to 65° C. at an appropriate pH, typically from pH 3 to 9 and preferably at a physiologically acceptable pH such as from pH 6.5 to 7.5.

The concentration of the compounds of the present invention in the compositions and medicaments depends on the compound's photosensitising ability and is preferably in the range from 0.0005 to 20% for topical use and from 100 μM to 30 mM for intravenous use.

Dry compositions and medicaments, which may be reconstituted before use, are also provided in the present invention. These may be prepared by dry mixing solid components of the composition or preparing a liquid composition which is evaporated to dryness generally under mild conditions under vacuum or in low temperature ovens, suitable techniques for drying include freeze drying.

According to a feature of the present invention there is provided a phenoselenazinium compound of Formula (1) for use in therapy wherein $R^1$-$R^8$, A and B, Q, Z, Y and p are as defined above.

According to a feature of the present invention there is provided a phenoselenazinium compound of Formula (1) for use as a medicament wherein $R^1$-$R^8$, A and B, Q, Z, Y and p are as defined above.

According to a feature of the present invention there is provided a phenoselenazinium compound of Formula (1) or a composition comprising one or more of the compounds for use in a treatment that removes, deactivates or kills unwanted tissues or cells, wherein $R^1$-$R^8$, A and B, Q, Z, Y and p are as defined above.

According to a feature of the present invention there is provided a phenoselenazinium compound of Formula (1) for use as an anti-cancer agent wherein $R^1$-$R^8$, A and B, Q, Z, Y and p are as defined above.

According to a feature of the present invention there is provided a phenoselenazinium compound of Formula (1) for use as an anti-infective agent wherein $R^1$-$R^8$, A and B, Q, Z, Y and p are as defined above.

The treatment may involve application of the compound or composition directly to the site in need of treatment or by systemic administration, the treatment preferably involves the use of PDT.

According to a feature of the present invention there is provided a use of a phenoselenazinium compound of Formula (1) in the manufacture of a medicament for the removal, deactivation or killing of unwanted cells or tissues, wherein $R^1$-$R^8$, A and B, Q, Z, Y and p are as defined above.

The medicaments may be used in treatments that remove, deactivate or kill unwanted cells or tissues, particularly for treatments where the medicament is used as an anti infective or as an anti cancer agent. The medicament may be applied directly to the site in need of treatment or by systemic administration; the treatment preferably involves the use of PDT.

Preferably the phenoselenazinium compound, composition or medicament comprising it is used in PDT as an anticancer agent, an antibacterial or an antifungal or an antiviral, in the treatment of dermatological, ophthalmic, cardiovascular, gynaecological and dental conditions and the prevention of infection. The uses may be in humans or animals. The phenoselenazinium compound may find particular use against antibiotic resistant bacteria.

For use in PDT, a compound must have at least some and preferably all of the following properties. Most importantly, it should cause the destruction of target tissues or cells (for example tumour cells or bacterial cells) efficiently on exposure to light (preferably wavelengths ca. 600-800 nm). The PDT treatment using the compound should show a high degree of selectivity between target and normal tissues and cells. The compound should have relatively little dark toxicity and it should cause little or no skin photosensitivity in the patient. The compound should have short drug to light intervals for patient and hospital convenience and to minimise treatment costs. The photosensitiser should be capable of being incorporated into pharmaceutically acceptable formulations and should be capable of being transported to the site requiring treatment.

In oncology, several different types of compound have been used to treat both solid tumours and thin tumours of hollow organs such as the oesophagus and bladder. However, the use of these compounds has been restricted partly because of lack of selectivity between tumour and healthy tissue and cells, and partly because of the prolonged skin photosensitivity which can be caused. There is a need for new compounds which cause little or no skin photosensitivity and which selectively destroy tumour cells.

Examples of uses of the compounds of the present invention are as photosensitising drugs for PDT to treat cancer and pre-cancerous conditions including Barrett's oesophagus and cervical intraepithelial neoplasia (CIN), bladder cancer, colon cancer, non-melanoma skin cancer, actinic keratoses, melanoma, brain-pituitary cancer, brain-glioma, pancreatic cancer, head and neck cancer, lung cancer, particularly non small cell, mesothelioma, oesophageal cancer, stomach cancer, cutaneous T-cell lymphoma. In addition to the above the compounds are used as photosensitising drugs for PDT in veterinary applications, for example in treatment of cancers such as ear cancer in cats, as antifungal, antibacterial and antviral treatments, for sterilisation of wounds in animals and for ophthalmological treatments in animals.

The present compounds demonstrate one or more of the following advantages in oncology:

Strong photoactivity.
Low absorption of light in the UV/blue region. This results in a lower propensity of the compounds to skin photosensitivity.
High selectivity for tumours.
Low dark toxicity.
Very short drug-to-light time interval compared with existing PDT drugs.

PDT using compounds of Formula (1) has not yet been used in clinical situations against infections caused by bacteria and other microorganisms. The use of antibiotics to treat bacterial infections is becoming challenging due to the increasing resistance of many bacterial species to commonly used antibiotics, such as tetracyclines and beta-lactams. Hospital-acquired antibiotic resistant infections such as MRSA are especially problematic. PDT in antibacterial treatment is a convenient and promising alternative to antibiotics for local treatment.

When developing antibacterial agents a major problem which must be overcome is the uptake of the drug into the bacterial cell. Gram negative and Gram positive bacteria differ in the composition of their outer surface and respond differently to antimicrobial agents, especially in terms of uptake. Due to the high negatively charged surface of Gram negative bacteria they are relatively impermeable to neutral or anionic drugs, including most commonly used photosensitisers. Development of antimicrobial compounds which are effective against Gram negative bacteria, as well as Gram positive bacteria would be highly beneficial to replace commonly used antibiotics and drugs which are becoming increasingly ineffective due to resistance. For uptake into Gram negative bacteria, it is accepted that the cationic derivatives are the most effective.

The compounds may be used in anti-microbial, antifungal and antiviral treatments, examples of uses include treatment and sterilisation of skin and wound infections such as burn wounds, for sterilisation of both recipient tissue and donated tissue during organ, including skin transplantation, in treatment of ulcers particularly leg or foot ulcers more particularly infected chronic leg or foot ulcers, nail infections; for parasitic infection, stomach infection, malaria, leprosy, for bacterial and fungal spore inactivation, for treatment of prions and viral infection such as HIV, for ear, nose and throat infections, tuberculosis, sexually transmitted diseases (STD's), herpes, for treatment of *Candida* localised infections for example of hair, nails and epidermis, such as tinea pedis and candida vulvovaginitis; and for use as infection preventatives such as sterilisation of surgical wounds, skin graft sterilisation, stem cell sterilisation, graft versus host disease; to treat ophthalmological conditions such as macular degeneration, occult choroidal neovascularisation (CNV), CNV due to pathological myopia, occult with age related macular degeneration (AMD), diabetic macular oedema, vascular problems such as cardiovascular disease, arteriosclerosis and restenosis and autoimmune diseases such as rheumatoid arthritis, skin diseases such as psoriasis, acne, vitiligo and eczema and other dermatological conditions such as hirsuitism, and sun damage, other benign conditions such as endometriosis and menorrhagia.

The compounds may also be used for other local infections as well as in the treatment of dental bacterial disease, such as gum abscesses, gum disease, gingivitis, and removal, deactivation or killing of plaque biofilms.

The present compounds demonstrate one or more of the following advantages in antimicrobial treatments:

Highly effective in deactivating a wide range of microorganisms, including Gram positive and Gram negative bacteria, including antibiotic resistant bacteria such as MRSA, and fungal infection.

Active against quiescent/stationary bacteria.

High selectivity for microorganisms with minimum damage to host tissue.

Unexpectedly low level of photobleaching.

The compound of Formula (1) is preferably used in treatments of localised and/or early cancer and/or pre-cancerous lesions in humans and in animals; or in the treatment and/or prevention of infections in wounds or skin in humans and animals.

For the above treatments the compounds of Formula (1) may be administered systemically or locally and where used in conjunction with PDT administration of the compound is followed by application of light of an appropriate dose and wavelength or wavelength range.

Where administered systemically the compounds may be delivered for example intravenously, orally, sub-cutaneously, intramuscularly, directly into affected tissues and organs, intraperitoneally, directly into tumours, intradermally or via an implant: The compounds may be delivered by injection or infusion.

Where administered locally or topically the compounds may be delivered via a variety of means for example via a spray, lotion, suspension, emulsion, gel, ointment, salves, sticks, soaps, liquid aerosols, powder aerosols, drops or paste.

Administration by any of the means described above may be repeated and typically from 1 to 20 treatments may be applied, more preferably from 1 to 5 treatments.

For the present compounds activation is by light, including white light, of an appropriate wavelength, preferably in the range from 600 to 800 nm, more preferably wavelengths are from 630 nm to 700 nm.

The light source may be any appropriate light source such as a laser, laser diode or non-coherent light source.

The light dose administered during PDT can vary but preferably is from 1 to 200 $J/cm^2$, more preferably from 20 to 100 $J/cm^2$.

Light exposure may be given at any time after a drug is initially administered or up to 48 hours after drug administration and the time may be tailored according to the condition being treated, the method of drug delivery and the specific compound used. Light exposure is preferably given at any time after a drug is initially administered up to 3 hours, more preferably from the time after a drug is initially administered up to 1 hour, especially up to 10 minutes.

Increased intensity of the light generally reduces exposure times.

It is preferred that exposure to light is localised to the area/region to be treated, and where tumours are being treated more preferably localised to the tumour itself. Continuous exposure to light of particular wavelengths may be achieved by use of a bandage that contains light elements within its structure.

The dose rates of the compounds of Formula (1) for intravenous administration to humans for oncology treatments are in the range 0.01 to 10 μmol (micromole)/kg, preferably in the range 0.1 to 2.0 μmol (micromole)/kg. To achieve a dose of say 2 μmol (micromole)/kg in a 70 kg patient requires injection of 70 ml of a 2 mM solution, or 5 ml at a concentration of 27 mM or 2.8 ml of a 50 mM solution. Typical injections volumes are in the range 0.1 to 100 ml, preferably from 5 to 50 ml.

The concentration used for bacterial cell kill in vitro is in the range from 0.1 to 100 μM, preferably from 1 to 50 μM and more preferably from 5 to 20 μM, especially 10 μM.

According to a further feature of the present invention there is provided a method of treatment of cancer and pre-cancerous conditions, the method comprising systemic administration (for example as a solution, suspension or emulsion) or applying to the area to be treated (for example by a spray, lotion, suspension, emulsion, ointment, gel or paste) a therapeutically effective amount of a compound of Formula (1) and optionally exposing the area to light to render active the compound, wherein in the compound of Formula (1) $R^1$-$R^8$, A and B, Q, Z, Y and p are as defined above.

According to a further feature of the present invention there is provided a method of treatment of microbial infections, burn wounds and other lesions and of dental bacterial disease, the method comprising systemic administration (for example as a solution, suspension or emulsion) or applying to the area to be treated (for example by a spray, lotion, suspension, emulsion, ointment, gel or paste) a therapeutically effective amount of a compound of Formula (1) and optionally exposing the area to light to render active the compound, wherein in the compound of Formula (1) $R^1$-$R^8$, A and B, Q, Z, Y and p are as defined above.

According to a further feature of the present invention there is provided a method of prevention of microbial infections, for example in wounds, surgical incisions, burn wounds, and other lesions and of dental bacterial disease, the method comprising systemic administration (for example as a solution, suspension or emulsion) or applying to the area to be treated (for example by a spray, lotion, suspension, emulsion, ointment, gel or paste) a therapeutically effective amount of a compound of Formula (1) and optionally exposing the area to light to render active the compound, wherein in the compound of Formula (1) $R^1$-$R^8$, A and B, Q, Z, Y and p are as defined above.

It is preferred that in the methods of treatment described above the area to which the compound of Formula (1) is applied or administered is exposed to light to render active the compound.

The compounds may be applied to prevent infection at any stage including wound contamination, where non-replicating organisms are present in a wound; wound colonisation where replicating microorganisms are present in a wound; and wound infection where replicating microorganisms are present that cause injury to the host. When there are >$10^5$ CFU/g tissue, it is more likely that sepsis will develop.

According to a further feature of the present invention there is provided a phenoselenazinium compound of Formula (1) or a composition comprising one or more of the compounds for use as a photodiagnostic agent and in photochemical internalisation, wherein in the compound of Formula (1) $R^1$-$R^8$, A and B, Q, Z, Y and p are as defined above.

Photochemical internalisation is the use of compounds to assist the uptake and subcellular localisation of drugs through their photosensitising properties and in non-therapeutic uses such as in photodiagnosis through their fluorescence properties. The latter approach takes advantage of the fact that the compound concentrates more in tumours than in surrounding healthy tissue and when induced to fluoresce (for example by application of blue light), the tumour fluoresces more strongly than the surrounding tissue. Examples of applications areas include diagnoses for oral diseases and for diseases of the bladder, lung and skin.

According to a further feature of the present invention the compounds of Formula (1) may be used as photoactivated antimicrobial, antifungal and antiviral agents for sterilisation of surfaces and fluids, wherein in the compound of Formula (1) $R^1$-$R^8$, A and B, Q, Z, Y and p are as defined above, for example they may be used to sterilise surgical implants and stents, particularly where these are coated or impregnated, to sterilise textiles such as bandages and dressings, IV lines and catheters, for sterilisation of water, air, blood, blood products, and food and food packaging to prevent transfer of infection, and for general household, hospital and office cleaning. The compounds are preferably used to sterilise surgical implants and stents, particularly where these are coated or impregnated, to sterilise textiles such as bandages and dressings, IV lines and catheters, for sterilisation of water, air, and food and food packaging to prevent transfer of infection, and for general household, hospital and office cleaning. The compounds may be applied to or contacted with the surfaces and fluids and activating the compound by exposure to light. Additionally the surface to be sterilised may be immersed in a mixture or solution of the compound or the fluid to be sterilised may be mixed with the compound or a solution or mixture containing the compound.

Furthermore, the present invention also provides a method of sterilising a surface or a fluid comprising contacting or applying the compound of Formula (1) or a composition comprising a compound of Formula (1) to the surface or fluid and optionally activating the compound by means of light. The compound may be contacted or applied by any means, for example as a spray, liquid, solution, suspension, foam, cream, gel or emulsion.

For applications in photosterilisation, a good compound must show a strong phototoxic effect in a wide range of microrganisms, ideally using ambient light, and should not photobleach readily.

In any of the uses described above the compounds of the present invention may be used advantageously in mixtures comprising two or more compounds of Formula (1) and in mixtures comprising one or more compounds of Formula (1) with one or more different therapeutic or active agents.

The compounds of Formula (1) in the compositions and medicaments described above, and those used in the treatments that remove, deactivate or kill unwanted tissues or cells are preferably compounds 1, 2, 3, 4, 5, 6 and 7.

The compounds of Formula (1) used as anti-cancer agents and in PDT treatment of cancer and pre-cancerous conditions are preferably compounds 1, 2, 4, 5 and 6.

The compounds of Formula (1) used as antimicrobials and in the method of treatment of microbial infections, burn wounds and other lesions and of dental bacterial disease are preferably compounds 1, 2, 3, 4, 6 and 7.

According to a further feature of the present invention there is provided a conjugate or composite formed between a compound of Formula (1) and a polymer, wherein in the compound of Formula (1) $R^1$-$R^8$, A and B, Q, Z, Y and p are as defined above.

The term composite as used herein refers to the situation wherein a compound of the invention is embedded in a polymer or physically occluded within or adsorbed onto a matrix or substrate. The polymer may be a biological polymer such as a peptide or a protein. Preferred polymers include those having anhydride and/or ester groups. Preferred compounds of Formula (1) which form a conjugate or composite with a polymer are those in which at least one of the Group A or B is a piperazinyl group.

In addition, the present invention provides a compound formed by the reaction between a compound of Formula (1) and a chlorotriazine derivative. The chlorotriazine derivative may be a polymer having chlorotriazine groups attached thereto.

Appropriate compounds of the present invention may be attached to polymeric surfaces, permanently by covalent bonds or reversibly by intermolecular interactions, thus affording a surface that can be sterilised whenever required by the application of light. This would be useful, for example, with intravenous lines in patients and in sutures and catheters and intravenous lines, where maintaining long-term sterility of the relevant surfaces is problematical. Resistance to photobleaching is an advantage in such applications, where prolonged stability of a chromophore is required.

Accordingly the present invention also provides an article having at least one surface to which is attached a compound of Formula (1).

Preferably the article is a medical device such as a venous, urinary or balloon catheter, suture, orthopaedic or artifical implant, heart valve, surgical screw or pin, pacemaker lead, feeding or breathing tube, vascular stent, intraocular lens, or small joint replacement. The article may also be of use in wound care and for packaging materials for medical use, for example, materials for medical equipment.

A compound of the present invention may be applied to or contacted with walls, floors and ceilings of hospitals, clinical surfaces such as operating tables, abattoirs, clean rooms in scientific laboratories, fibres which may be converted into woven, knitted or non-woven textile articles such as cleaning cloths, wipes, surgical gowns, bed linen, wound dressings and bandages. The compound may be applied directly or via attachment to a polymeric species.

Where the compound is to be applied to walls, floors, ceilings, and work surfaces, it is envisaged that it will be used as a component of a paint or lacquer, which comprises the compound, film forming polymers, which may or may not be cross-linkable, and an appropriate solvent, optionally with drying agents and other colorants. The surface coating may take the form of a solution or water-based dispersion.

Where compound or polymer is applied to walls, floors, ceilings this may be via a surface coating such as a paint.

Alternatively the article is one for use in the food and beverage industry and may be an item of packaging, a wrapper or storage carton or a piece of processing equipment.

The article may be a refrigerator, vending machine, ice making machine, a piece of restaurant equipment or other kitchen appliance.

According to a further feature of the present invention there is provided a method for sterilising fluids in which the fluid is contacted with a compound of Formula (1) or with a conjugate or composite formed between a compound of Formula (1) and a polymer whilst the compound or the conjugate or composite is illuminated, wherein in the compound of Formula (1) $R^1$-$R^8$, A and B, Q, Z, Y and p are as defined above.

The fluid may be a liquid or a gas or a vapour. The method may for example be applied to sterilisation of liquids, for example for sterilisation of water, or liquids used medically such as parenteral liquids for example saline or glucose and particularly for sterilisation of biological liquids such as blood, blood products, red cells, bone marrow cells, and stem cells. The method may also be applied to sterilisation of gases such as air, particularly air used in air conditioning systems, and oxygen used medically. This method is particularly useful for sterilising materials which cannot be easily sterilised by filtration methods.

The method is used preferably for sterilisation of water, or liquids used medically such as parenteral liquids such as saline or glucose and for sterilisation of biological liquids such as bone marrow cells and stem cells.

The compounds of Formula (1) and its conjugates or composites may be used as is, preferably with its surface area maximised such as in a finely divided form or in the form of beads or plates, or it may be used on or associated with any support material which provides a large surface area such as glass, glass wool, ceramics, plastics, metals and metal oxides. The support material is preferably transparent to light or allows light to pass through it. Where a support material is used this is arranged to maximise the surface area covered by the conjugate or composite and may be in the form of beads, plates, large surface areas in columns or tubes, foams or fibres.

The compound of Formula (1) or conjugate or composite is preferably continuously illuminated at the wavelengths and at the light doses described above.

The preferred compounds of Formula (1) are those preferred in this sterilisation method.

In a particular embodiment of this aspect of the invention the compound of Formula (1) or its conjugate or composite either alone or on a support material is packed into a column, typically made of a material which is transparent to light, such as silica glass or synthetic fibres. The fluid requiring sterilisation is passed into one end of the column, the whole column is continuously illuminated and sterilised material flows out from the other end of the column.

EXAMPLES

Example 1

Preparation of Phenoselenazine Starting Material

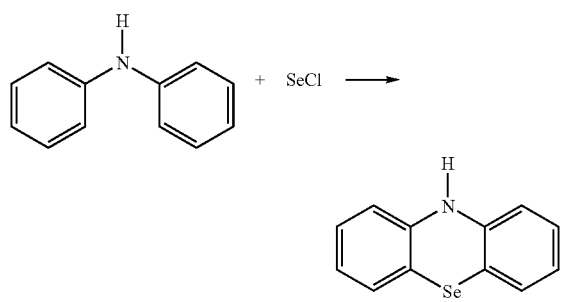

To a suspension of selenium monochloride (3.6 g, 0.016 mole) in toluene (50 cm$^3$) was added, over one hour, a solution of diphenylamine (5.5 g, 0.033 mole) in toluene (100 cm$^3$). Once the addition was complete, the reaction was refluxed for five hours. After this time, the reaction mixture was steam distilled to remove unreacted diphenylamine. The solid thus obtained was recrystallised from toluene. The product was identified by its melting point. Yield=20%

Compound 1:
3,7-Bis-(N,N-dibutylamino)phenoselenazin-5-ylium bromide

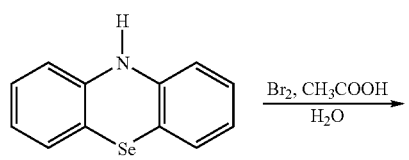

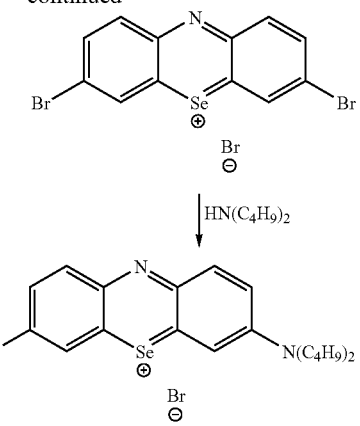

To a stirred solution of phenoselenazine (1.00 g) in glacial acetic acid (170 cm$^3$), under nitrogen and cooled in an ice-bath was added a solution of bromine (10 cm$^3$) in glacial acetic acid (10 cm$^3$). After 10 minutes the reaction mixture was poured into rapidly stirred water (400 cm$^3$). The resultant 3,7-dibromo-phenoselenazin-5-ylium bromide was deposited as a dark solid and was collected by filtration, washed with diethyl ether and dried. A portion of the product (1.24 g) was added to a vigorously stirred solution of dibutylamine (5.00 g) in dichloromethane (200 cm$^3$) under an atmosphere of nitrogen. The reaction mixture was stirred for 18 hours and then washed successively with water, dilute aqueous hydrobromic acid (5% w/w) and finally water. The organic phase was dried (MgSO$_4$) and the solvent removed by rotary evaporation. Flash column chromatography over silica gel 60 A was performed on the crude material using a mobile phase of chloroform with increasing methanol content to a maximum of 2%. 3,7-Bis-(N,N-dibutylamino)-phenoselenazin-5-ylium bromide was isolated as a dark blue solid in 17% yield.

Mass spectrum (electrospray in methanol) m/z=499.62. λmax (methanol)=664 nm, log ε=4.61.

Singlet oxygen yield in methanol (relative to Methylene Blue)=0.9

Partition coefficient (2-octanol/0.1 M aqueous potassium phosphate at pH 7): log P=>2.

Compound 2:
3,7-Bis-(N,N-dipropylamino)phenoselenazin-5-ylium iodide

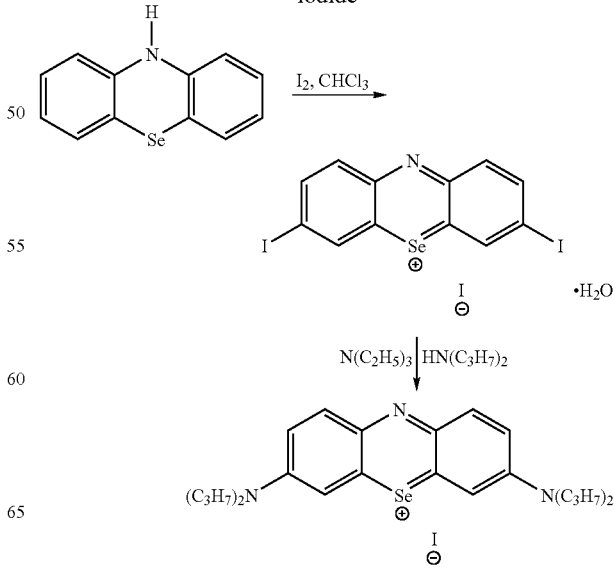

To a solution of phenoselenazine (1.03 g) in chloroform (60 cm³) cooled to <5° C. was added, over 90 minutes, a solution of iodine (3.11 g) in chloroform (100 cm³). Following the addition, the reaction was stirred for a further 30 minutes before filtration. 3,7-Diiodo-phenoselenazin-ylium iodide hydrate was collected, washed with copious volumes of chloroform and dried.

To a solution of 3,7-diiodo-phenoselenazin-ylium iodide hydrate (2.85 g) in methanol (300 cm³) was added triethylamine (1.0 cm³) followed by dipropylamine (3.69 g). The reaction was stirred for 24 hours. The residue remaining after removal of the methanol was taken up in dichloromethane and washed with dilute hydriodic acid (4% w/w) followed by water. The organic phase was isolated and dried ($MgSO_4$). After removal of the dichloromethane, the residue was taken up in a minimum volume of acetone and the product precipitated by the addition of a large excess of petroleum ether 60-80° C. The product was collected by filtration, washed with petroleum ether 60-80° C. and dried, giving 3,7-bis-(N,N-dipropylamino)phenoselenazin-5-ylium iodide as a dark blue powder in 23% yield.

Mass spectrum (electrospray/methanol) m/z=444.2
λmax (methanol)=666 nm, log ϵ=4.62
Singlet oxygen yield (relative to MB)=1.1
Log P=>2

Compound 3:
3,7-Bis-(N,N-diethylamino)phenoselenazin-5-ylium iodide

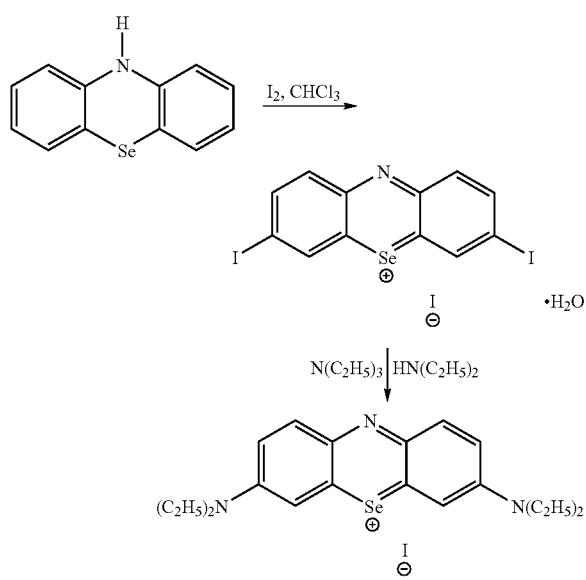

To a solution of 3,7-diiodo-phenoselenazin-ylium iodide hydrate (prepared as above for Compound 2) (2.83 g) in methanol (300 cm³) was added triethylamine (1.0 cm³) followed by diethylamine (10 cm³). The reaction was stirred for 48 hours. The residue remaining after removal of the methanol was taken up in dichloromethane and washed with dilute hydriodic acid (5% w/w) followed by water. The organic phase was isolated and dried ($MgSO_4$). Flash column chromatography over silica gel 60 Å was performed on the crude material using a mobile phase of 85/15 methanol/water containing 3% w/v ammonium acetate. After isolation of the desired fractions and removal of the methanol, the product was extracted from the aqueous phase using dichloromethane. Concentration of the dichloromethane in vacuo and addition of an excess of diethyl ether resulted in precipitation of the product. The product was collected by filtration, washed with diethyl ether and dried to give 3,7-bis-(N,N-diethylamino)-phenoselenazin-5-ylium iodide as a dark blue powder, in 22% yield.

Mass spectrum (electrospray/methanol) m/z=388.1
λmax (methanol)=660 nm, log ϵ=4.80
Singlet oxygen yield (relative to MB)=1.5
Log P=1.5

Compound 4:
3,7-Bis-(N,N-dipentylamino)phenoselenazin-5-ylium iodide

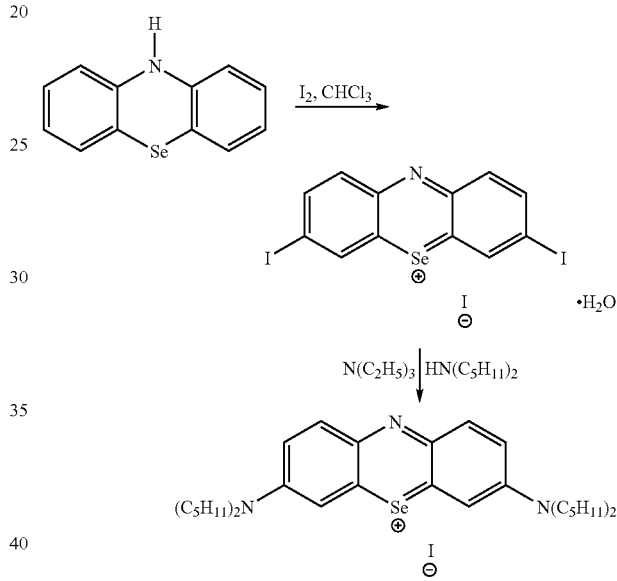

To a solution of 3,7-diiodo-phenoselenazin-ylium iodide hydrate (2.49 g) (prepared as above for Compound 2) in methanol (300 cm³) was added triethylamine (1.0 cm³) followed by dipentylamine (10 cm³). The reaction was stirred for 48 hours. The residue remaining after removal of the methanol was taken up in dichloromethane and washed with dilute hydriodic acid (5% w/w) followed by water. The organic phase was isolated and dried ($MgSO_4$). Flash column chromatography over silica gel 60A was performed on the crude material using a mobile phase of 85/15 methanol/water containing 3% w/v ammonium acetate. After isolation of the desired fractions and removal of the methanol, the product was extracted from the aqueous phase using dichloromethane. Concentration of the dichloromethane in vacuo and addition of an excess of diethyl ether resulted in precipitation of the product. The product was collected by filtration, washed with diethyl ether and dried to give 3,7-bis-(N,N-dipentylamino)-phenoselenazin-5-ylium iodide as a dark blue powder in 17% yield.

Mass spectrum (electrospray, methanol) m/z=556.3
λmax (methanol)=668 nm log ϵ=4.70
Singlet oxygen yield (relative to MB)=1.4
Log P=>2

Compound 5: 3,7-Bis-(N,N-dihexylamino)phenoselenazin-5-ylium iodide

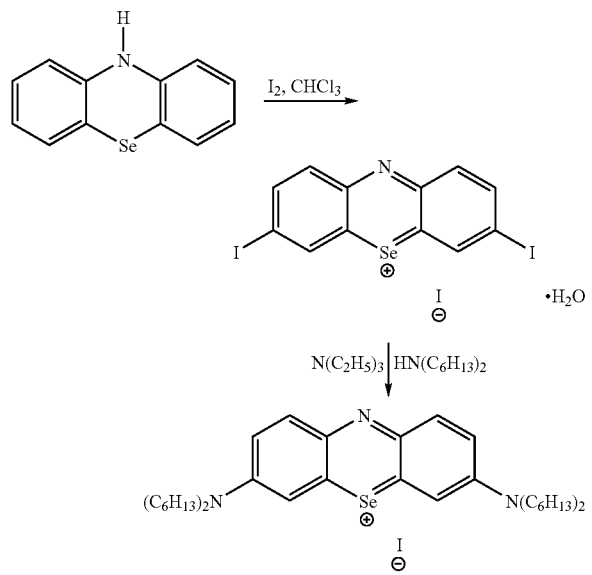

To a solution of 3,7-diiodo-phenoselenazin-ylium iodide hydrate (2.34 g) (prepared as above for Compound 2) in methanol (300 cm³) was added triethylamine (1.0 cm³) followed by dihexylamine (5 cm³). The reaction was stirred for 24 hours. The residue remaining after removal of the methanol was taken up in dichloromethane and washed with dilute hydriodic acid (5% w/w) followed by water. The organic phase was isolated and dried (MgSO₄). Flash column chromatography over silica gel 60 Å was performed on the crude material using a mobile phase of 85/15 methanol/water containing 3% w/v ammonium acetate. After isolation of the desired fractions and removal of the methanol, the product was extracted from the aqueous phase using dichloromethane. Concentration of the dichloromethane in vacuo and addition of an excess of diethyl ether resulted in precipitation of the product. The product was collected by filtration, washed with diethyl ether and dried to give 3,7-bis-(N,N-dihexylamino)-phenoselenazin-5-ylium iodide as a dark coloured powder, in 21% yield.

Mass spectrum (electrospray/methanol) m/z=612.5

$\lambda$max (methanol)=670 nm, log $\epsilon$=4.12

Singlet oxygen yield (relative to MB)=1.1

Log P=>2

Compound 6: 3-N,N-dibutylamino-7-N,N-dipropylamino-phenoselenazin-5-ylium iodide

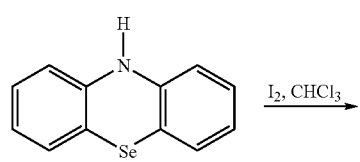

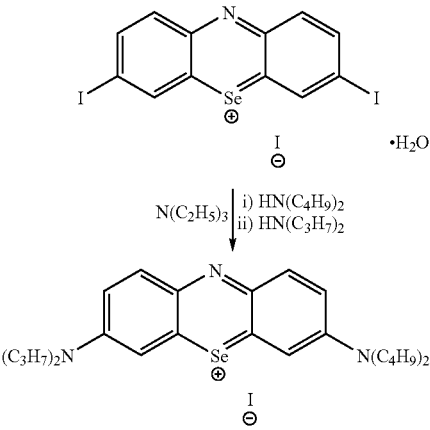

To a solution of 3,7-diiodo-phenoselenazin-ylium iodide hydrate (1.27 g) (prepared as above for Compound 2) in dichloromethane (250 cm³) was added a solution of dibutylamine (0.25 g) in dichloromethane (25 cm³). The reaction was stirred for 48 hours. The presence of the mono-substituted compound was determined by thin layer chromatography. Following this, to the reaction mixture was added a solution of dipropylamine (0.21 g) in dichloromethane (25 cm³). The reaction was stirred for 24 hours. After this time, reaction progress was again monitored by thin layer chromatography. Further additions of dipropylamine in dichloromethane were continued until no further mono-substituted material could be detected. The reaction mixture was then washed with dilute hydriodic acid (1% w/w) followed by water. The organic phase was isolated and dried (MgSO₄). Concentration of the dichloromethane in vacuo followed by addition of a large excess of diethyl ether yielded a precipitate. The precipitate was collected by filtration, washed with diethyl ether and dried to give 3-N,N-dibutylamino-7-N,N-dipropylamino-phenoselenazin-5-ylium iodide as a dark blue solid, in 18% yield.

Mass spectrum (electrospray/methanol) m/z=472.3

$\lambda$max (methanol)=666 nm, log $\epsilon$=4.72

Singlet oxygen yield (relative to MB)=1.1

Log P=>2.

Compound 7: Mixture of 1-methoxy-3-N,N-dibutylamino-7-N,N-dipropylamino-phenoselenazin-5-ylium iodide and 9-methoxy-3-N,N-dibutylamino-7-N,N-dipropylamino-phenoselenazin-5-ylium iodide This mixture was prepared as described above for Compound 6 except that methanol was used as solvent instead of chloroform.

Comparative compound A: 3,7-N,N-dimethylamino-phenoselenazin-5-ylium iodide 3,7-N,N-dimethylamino-phenoselenazin-5-ylium iodide may be prepared by the method described above in Example 3 but using dimethylamine instead of diethylamine.

Photoinactivation of Bacteria by Phenoselenazinium Derivates

Materials and Methods

Photosensitiser 1 mM stock solutions of the photosensitisers were made up by solubilising the photosensitiser in dimethyl sulfoxide.

Bacteria

Bacteria (*E. coli*, *S. aureus*) and yeast (*C. albicans*) cells were grown at 37° C. until the cells reached the logarithmic growth phase. Bacterial cells were grown in nutrient media, yeast cells were grown in Sabouraud media (obtainable via Millipore Limited, Watford, England).

Following the incubation, the log phase cells were washed twice in 0.1 M pH7.0 potassium phosphate buffer. The cells were then resuspended in buffer to give $3.5 \times 10^8$ CFU/ml for *E. coli* and *S. aureus*, or $1.0 \times 10^7$ CFU/ml for *C. albicans*.

Photodynamic Treatment

The cells were incubated for 30 min at 37° C. with 10 µM photosensitiser. Following the incubation 2 mL of the cell suspension was removed into a 30 mm sterile Petri dish. The cell containing dish was then illuminated with a 665 nm Ceramoptec diode laser (trade mark of Ceramoptec GmBH, Germany and obtainable from Biolitec, Germany), at a light dose of 3 J/cm² (10 mW/cm²).

Cell Survival Analysis

Cells of the illuminated and non illuminated cultures were serially diluted and plated on either: nutrient agar (*E. coli* and *S. aureus*) or sabouraud agar (*C. albicans*). The plates were incubated for 24 h (*E. coli* and *C. albicans*) or 48 h (*S. aureus*). The colonies on the plates were counted as a measure of cell survival.

TABLE 1

Log change in CFU/mL

| Photosensitiser | S. aureus | E. coli | C. albicans |
|---|---|---|---|
| Compound A | 1.74 (0.41) | 3.33 (0.01) | 0.19 (0.06) |
| Compound 3 | 2.72 (0.87) | 3.78 (0.28) | 0.16 (0.22) |
| Compound 2 | 1.70 (0.48) | 3.16 (0.03) | 0.35 (0.42) |
| Compound 1 | 0.21 (0.01) | 5.48 (0.34) | 0.00 (0.05) |
| Compound 4 | 0.95 (0.73) | 3.66 (2.23) | 0.17 (0.02) |
| Compound 5 | 0.18 (0.12) | 0.02 (0.13) | −0.03 (0.03) |
| Compound 6 | 2.66 (2.26) | 6.54 (0.00) | 6.12 (0.82) |
| Compound 7 | 2.31 (0.69) | 3.47 (0.94) | 0.59 (0.69) |

Anti-Tumour Efficacy in vivo

Tumour destruction was assessed in CBA/gy mice bearing subcutaneous CaNT tumours. The photosensitiser was administered intravenously at doses up to 16.7 µmol/kg. At various times after photosensitiser administration, the tumour was illuminated superficially with 60 J/cm², 50 mW/cm² light from a Paterson lamp using a 660±15 nm filter. Drug-light intervals ranged from 0 h (in practice, 1-2 minutes) up to 96 h. 72 h after illumination a cross sectional slice was removed from the centre of the tumour parallel to the incident light, an image of this was captured and the macroscopic necrotic area quantified using image analysis software. Necrosis was expressed as % area of the total tumour slice. % tumour necrosis in control tumours was generally <10%.

An arbitrary score 0-3 of the severity of damage to normal tissues surrounding the tumour (usually kidney) was also recorded. 0=no detectable damage; 1=minimal damage to one organ; 2=damage to more than one organ; 3=death The phenoselenazinium compounds were dissolved and administered in a composition comprising 25% Solutol, 10% ethanol, 65% saline vehicle.

TABLE 2

Summary of anti tumour performance in vivo

| Photosensitiser | Dose µmol/Kg | Drug to light interval/h | % tumour necrosis | Normal tissue damage |
|---|---|---|---|---|
| Compound 1 | 0.84 | 0 | 93 | 1 |
| Compound 1 | 0.84 | 1 | 40 | 0 |
| Compound 1 | 1.67 | 0 | 88 | 1.5 |
| Compound 1 | 1.67 | 1 | 88 | 1.2 |
| Compound 2 | 1.67 | 0 | 55 | 0 |
| Compound 2 | 8.4 | 0 | 87 | 1 |
| Compound 2 | 8.4 | 1 | 17 | 0 |
| Compound 2 | 16.7 | 0 | 100 | 2 |
| Compound 3 | 1.67 | 0 | 0 | 0 |
| Compound 3 | 1.67 | 1 | 0 | 0 |
| Compound 4 | 1.67 | 0 | 10 | |
| Compound 4 | 4.18 | 0 | 45 | |
| Compound 4 | 6.26 | 0 | 80 | 0 |
| Compound 4 | 8.34 | 0 | 80 | 1 |
| Compound 5 | 1.67 | 0 | 0 | 0 |
| Compound 5 | 8.4 | 1 | 30 | 0 |
| Compound 6 | 1.67 | 0 | 75 | 0 |
| Compound 6 | 1.67 | 1 | 15 | 0 |
| Compound A | 1.67 | 0 | 0 | 0 |
| Compound A | 1.67 | 1 | 0 | 0 |

Although any methods and materials, similar or equivalent to those described herein, can be used in the practice or testing of the present invention, the preferred methods and materials are described herein. All publications, patents and patent applications cited herein are incorporated herein by reference for the purpose of disclosing and describing specific aspects of the invention for which the publication is cited.

The invention claimed is:

1. A phenoselenazinium compound of Formula (1):

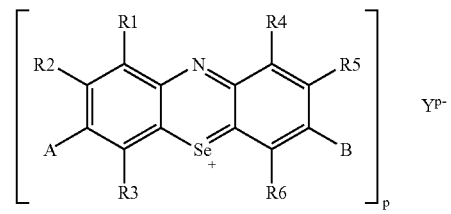

Formula (1)

wherein:

$R^1$-$R^6$ are each independently selected from H, optionally substituted $C_{1-12}$-alkyl, optionally substituted $C_{1-12}$-alkoxy, F, Cl, Br and I;

A and B are each independently selected from:

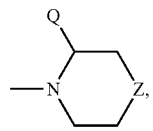 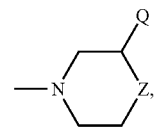

-continued

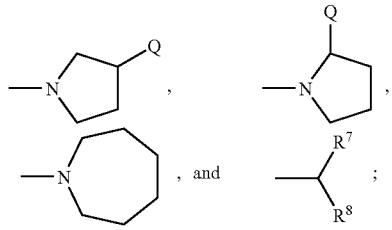

Q is selected from H and optionally substituted $C_{1-12}$-alkyl;
Z is selected from $C(R^a)_2$, O, S, $SO_2$, and $NR^a$, in which each $R^a$ is independently selected from H and optionally substituted $C_{1-12}$-alkyl;
$R^7$ and $R^8$ are each independently selected from H and optionally substituted $C_{1-12}$-alkyl;
Y is a counteranion; and
p is 1, 2 or 3,
wherein the optional substituents for the alkyl and alkoxy groups represented by $R^1$ to $R^8$, $R^a$ and Q are selected from Ph, F, Cl, Br, I, OH, $OC_{1-4}$-alkyl, CN, $OCOC_{1-4}$-alkyl, optionally substituted $C_{3-6}$-cycloalkyl, COOH, $COOC_{1-4}$-alkyl and $SO_3H$, with the proviso that the compound is not
3,7-bis(4-methyl-1-piperazinyl)phenoselenazinium dichloride,
3,7-bis(N,N-dimethylamino)-phenoselenazin-5-ium chloride,
3,7-diamino-phenoselenazin-5-ium chloride,
the corresponding bromides and iodides, or
the compound in which $R^1$ to $R^4$, and $R^6$ are all H, $R^5$ is methyl, A is $NMe_2$ and B is $NH_2$.

2. A compound according to claim 1 wherein A and B are each independently of the formula:

in which $R^7$ and $R^8$ are each independently optionally substituted, open chain $C_{1-12}$-alkyl.

3. A compound according to claim 1 or claim 2 in which $R^1$-$R^6$ are each independently selected from H and $C_{1-12}$-alkoxy.

4. A compound according to claim 3 in which $R^7$ and $R^8$ are each independently $C_{2-5}$-alkyl.

5. A pharmaceutical composition comprising one or more compounds of Formula (1) as defined in claim 1 and a pharmaceutically acceptable diluent or excipient.

6. A compound of Formula (1) wherein:
$R^1$-$R^6$ are each independently H;
A and B are both:

in which:
$R^7$ and $R^8$ are both ethyl, n-propyl, n-butyl or n-pentyl;
Y is a counteranion; and
p is 1, 2 or 3.

7. A compound of Formula (1) wherein:
$R^1$ or $R^4$ is H or methoxy, provided one of $R^1$ or $R^4$ is methoxy;
$R^2$, $R^3$, $R^5$ and $R^6$ are H
A is

in which:
$R^7$ and $R^8$ are both n-propyl; and
B is

in which:
$R^7$ and $R^8$ are both n-butyl;
Y is a counteranion; and
p is 1, 2 or 3.

* * * * *

UNITED STATES PATENT AND TRADEMARK OFFICE
CERTIFICATE OF CORRECTION

| | | |
|---|---|---|
| PATENT NO. | : 7,407,948 B2 | Page 1 of 1 |
| APPLICATION NO. | : 11/723522 | |
| DATED | : August 5, 2008 | |
| INVENTOR(S) | : John Griffiths et al. | |

It is certified that error appears in the above-identified patent and that said Letters Patent is hereby corrected as shown below:

On the Title Page Item (63) should read

Related U.S. Application Data

(63)  Continuation-in-part of Application No. PCT/GB05/03558, filed on September 14, 2005

On the Title Page Item (30) should read

Foreign Application Priority Data

(30)  September 20, 2004  (GB)  . . . . . . . . . . . . . . . . . . . . .  0420893.0

Signed and Sealed this

Second Day of December, 2008

JON W. DUDAS
*Director of the United States Patent and Trademark Office*